United States Patent [19]
Moeller et al.

[11] Patent Number: 4,549,032
[45] Date of Patent: * Oct. 22, 1985

[54] PROCESS FOR PRODUCING STYRENE

[75] Inventors: Friedrich-Wilhelm Moeller, Friedrichsdorf; Henning Buchold, Maintal; Helmut Klein, Hanau am Main; Otto-Ludwig Garkisch, Bad Soden; Friedrich Guetlhuber, Metten; Walter Laber, Deggendorf, all of Fed. Rep. of Germany

[73] Assignees: Metallgesellschaft Aktiengesellschaft, Frankfurt; Deggendorfer Werft und Eisenbau GmbH, Deggendorf, both of Fed. Rep. of Germany

[*] Notice: The portion of the term of this patent subsequent to Sep. 1, 1998 has been disclaimed.

[21] Appl. No.: 613,595

[22] Filed: May 23, 1984

[30] Foreign Application Priority Data

May 26, 1983 [DE] Fed. Rep. of Germany ....... 3319024

[51] Int. Cl.$^4$ ............................................. C07C 5/36
[52] U.S. Cl. .................................... 585/445; 585/440; 585/442; 585/444
[58] Field of Search ............... 422/200, 201; 585/440, 585/445, 444, 442; 423/DIG. 12

[56] References Cited

U.S. PATENT DOCUMENTS

| 3,100,807 | 8/1963 | Hatfield et al. | 585/440 |
| 3,158,564 | 11/1964 | Cole | 585/440 |
| 3,690,839 | 9/1972 | Jones | 585/440 |
| 3,807,963 | 4/1974 | Smith | 585/444 |
| 4,229,603 | 10/1980 | Lyon | 585/444 |
| 4,287,375 | 8/1981 | Moeller et al. | 585/440 |

Primary Examiner—D. E. Gantz
Assistant Examiner—A. Pal
Attorney, Agent, or Firm—Karl F. Ross; Herbert Dubno

[57] ABSTRACT

A process for producing styrene by the dehydrogenation of ethyl benzene whereby the ethyl benzene in a mixture with steam is introduced into a tubular reactor, the tubes of which are heated by molten salts. The structural parameters of this process are the tube diameter which should be 20 to 35 millimeters, the temperature of the molten salts which should be 580° to 660° C. and at most 20° C. higher than the reaction temperature at the catalyst and the weight ratio of steam to ethyl benzene of the feed stock which should be 0.5 to 1. The process saves energy and increases efficiency by reducing the steam consumption.

10 Claims, 1 Drawing Figure

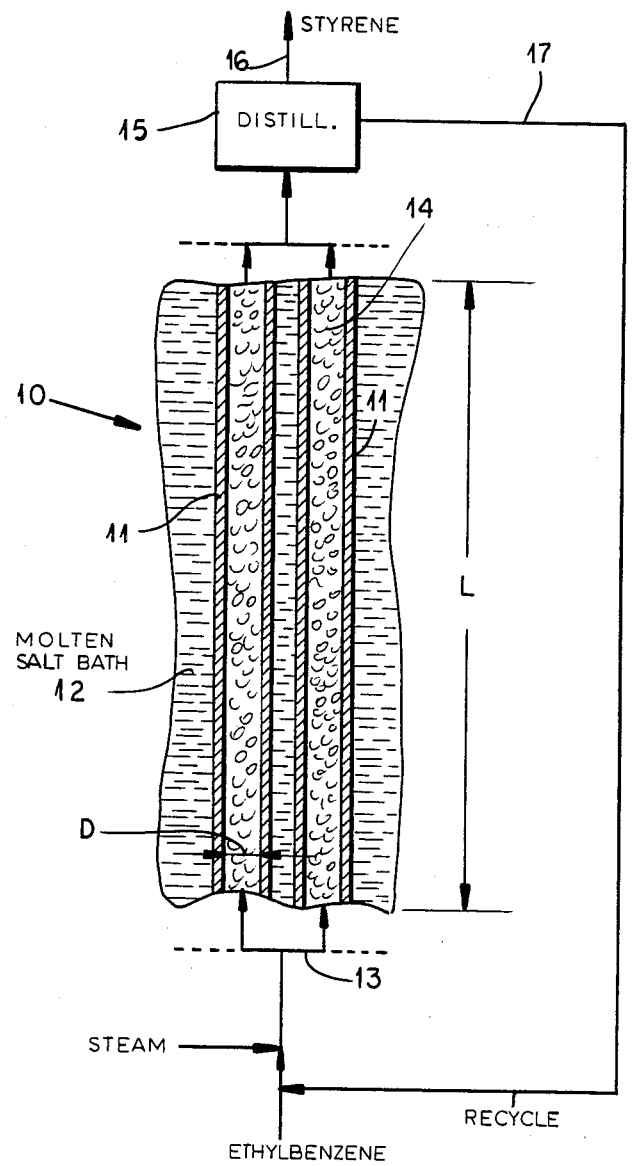

PROCESS FOR PRODUCING STYRENE

FIELD OF THE INVENTION

Our present invention relates to a process for producing styrene and, more particularly, to a process for the production of styrene by the dehydrogenation of ethyl benzene.

BACKGROUND OF THE INVENTION

From German Pat. No. 2,909,763 and the corresponding U.S. Pat. No. 4,287,375, it is known to dehydrogenate ethyl benzene by passing a mixture thereof with steam into contact with a catalyst in a tube reactor indirectly heated by molten salts. This process is carried out at a pressure of 0.3 to 1 bar, at a temperature of 580° to 660° C. of the molten salts, a temperature which is not more than 20° C. above the reaction temperature at the catalyst. The steam and ethyl benzene are supplied to the tubes of the reactor in a weight ratio of 1.2 to 1.5.

While this process has proved to be successful, modern energy economics requires minimization of the steam consumption and maximization of the conversion of ethyl benzene to styrene.

OBJECTS OF THE INVENTION

It is, therefore, the principal object of the present invention to improve upon the method described in U.S. Pat. No. 4,287,375 by reducing the consumption of steam and increasing the conversion of ethyl benzene to styrene, or ensuring a high conversion of ethyl benzene to styrene.

Another object of the invention is to improve upon the energy economics of a process for dehydrogenating ethyl benzene to form styrene.

SUMMARY OF THE INVENTION

We have now discovered, quite surprisingly, that it is possible to reduce the consumption of steam and yet achieve a high conversion of ethyl benzene to styrene when the inside diameter of the catalyst containing tubes is reduced below the tube diameters used heretofore to a critical range of inside diameters and, simultaneously, a reduced ratio of steam to ethyl benzene is used. More specifically, we have found that when the inside diameter of the catalyst containing tubes is in the range of substantially 20 to 35 mm and the weight ratio of steam to ethyl benzene is 0.5 to 1, it is possible to effect a conversion of 65 to 75 mole percent ethyl benzene to styrene.

The catalyst used according to the invention are continuously available dehydrogenation catalysts consisting of substantially 50-80% iron oxide, 2-10% chromium oxide and the balance alkali, e.g. sodium or potassium oxide or hydroxide.

One of the characteristic features of the invention is the consumption of steam per kilogram of styrene product. This can be 0.75 to 1.4 kilograms of steam per kilogram of styrene produced with this present invention, and the process's high selectivity in spite of the reduced steam consumption because 93 to 96 mole percent of the reacted ethyl benzene is transformed to styrene so that byproduct production occurs in only small quantities.

Preferably the mixture of steam and ethyl benzene supplied to the catalyst containing tubes is in a weight ratio of 0.6 to 0.9 and the consumption of steam is about 0.9 to 1.2 kilograms per kilogram of product styrene. In the earlier process, the mixture supplied to the catalyst containing tubes contained steam and ethyl benzene in a weight ratio of 1.2 to 1.5 and the steam consumption as 1.85 to 2 kilograms of steam per kilogram of styrene product. The tube diameter has been found to be critical in conjunction with the reduced ratio of steam to ethyl benzene and with larger diameters of the tubes or smaller diameters of the tubes from the range of 20 to 35 mms, either product selectivity or conversion falls off markedly.

The molten salts which are used to indirectly heat the catalyst preferably consist of a mixture of carbonates of sodium, potassium and lithium. The molten salt mixture prevents corrosion of the tubes and has high stability.

BRIEF DESCRIPTION OF THE DRAWING

The above and other objects, features and advantages of the present invention will become more readily apparent from the following description, reference being made to the accompanying drawing, the sole FIGURE of which illustrates the process of the invention.

SPECIFIC DESCRIPTION AND EXAMPLES

In the drawing, we have diagrammatically shown the single stage reactor 10 in which the reaction is to be carried out, i.e. the ethyl benzene is to be subjected to an isothermal dehydrogenation.

The tubes 11 of the reactor are indirectly heated by the hot molten salts of the bath 12 and mixed feed stocks consisting of steam and ethyl benzene are supplied to the tubes as indicated at 13. The tubes are being filled with the iron oxide based catalyst 14.

The product withdrawn from the tubular reactor 10 is separated by distillation at 15 to form a first stream 16 which contains styrene and the small amount of any byproducts which are produced.

The second stream 17 which contains unreacted ethyl benzene is recycled as illustrated at the inlet to the tubular reactor.

Apparently the invention is effective largely because the dehydrogenation of ethyl benzene in the tubular reactor is highly dependent on temperature and the high yields required are a result of the fact that the heat required for the reaction can be supplied uniformly, while hot spots are avoided, because the catalyst containing tubes are small in diameter.

EXAMPLES

The process according to the invention is tested in a pilot plant. Styrene is produced from a mixture of steam and ethyl benzene in contact with 1.5 liters of a commercially available catalyst in a tubular reactor, in which the catalyst-containing tube has a length of 3 meters and an inside diameter of 25 mm. The catalyst consists of 70% iron oxide, 8% chromium oxide and the balance sodium oxide. Ethyl benzene is caused to flow in contact with the catalyst at a rate of 1.5 liters per hour. The pressure at the outlet of the reactor is 0.5 bar. The molten salt bath consists of a mixture of carbonates of sodium, potassium and lithium and is at a temperature of 620° C. The mixed feedstocks are preheated to 540° C. and are caused to flow in contact with the catalyst in one case in a weight ratio of 0.6 and in another case in a weight ratio of 0.8 of steam to ethyl benzene. The results obtained have been compiled in the subsequent table, in which the conversion is defined as the quotient of the converted quantity and the supplied quantity of ethyl benzene and the selectivity is defined as the quotient of the quantity of styrene product and the quantity of reacted ethyl benzene.

| Ratio of steam and ethyl benzene in mixed feedstocks (kg/kg) | 0.6 | 0.8 |
|---|---|---|
| Ratio of steam and styrene product (kg/kg) | 0.89 | 1.1 |
| Conversion (mole percent) | 67.5 | 72.8 |
| Selectivity (mole percent) | 94.9 | 93.8 |
| The product consists of | | |
| Ethyl benzene (wt. %) | 32.5 | 27.2 |
| Styrene (wt. %) | 62.4 | 66.9 |
| Toluene (wt. %) | 3.4 | 3.9 |
| Benzene (wt. %) | 1.3 | 1.7 |
| High-boiling residue (wt. %) | 0.4 | 0.3 |

We claim:

1. A process for the production of styrene by the dehydrogenation of ethyl benzene which comprises the steps of:
   (a) feeding a mixture of steam and ethyl benzene in a weight ratio of 0.5 to 1, to reactor tubes of a tube reactor, the inside diameter of said tubes being between 20 and 35 millimeters, said reactor tubes containing a dehydrogenation catalyst;
   (b) heating said tubes and indirectly heating the catalyst contained therein by a molten salt bath having a temperature in the range of 580° C. to 660° C., the temperature of said bath being not more than 20° C. in excess of the reaction temperature at said catalyst; and
   (c) effecting a dehydrogenation reaction of said ethyl benzene on said catalyst to convert 65 to 75 mole percent of the ethyl benzene of said mixture to styrene.

2. The process defined in claim 1 wherein steam is supplied to said tubes in a ratio such that the weight ratio of steam supplied to styrene produced is 0.75 to 1.4.

3. The process defined in claim 2 wherein 93 to 96 mole percent of the ethyl benzene reacted on said catalyst is converted to styrene.

4. The process defined in claim 1 wherein said mixture has a weight ratio of steam to ethyl benzene of 0.6 to 0.9.

5. The process defined in claim 1 wherein the weight ratio of the steam to the styrene product is substantially 0.9 to 1.2.

6. The process defined in claim 2 wherein said mixture has a weight ratio of steam to ethyl benzene of 0.6 to 0.9.

7. The process defined in claim 2 wherein the weight ratio of the steam to the styrene product is substantially 0.9 to 1.2.

8. The process defined in claim 3 wherein said mixture has a weight ratio of steam to ethyl benzene of 0.6 to 0.9.

9. The process defined in claim 3 wherein the weight ratio of the steam to the styrene product is substantially 0.9 to 1.2.

10. The process defined in claim 4 wherein the weight ratio of the steam to the styrene product is substantially 0.9 to 1.2.

* * * * *